US010425466B2

(12) United States Patent
Salinas et al.

(10) Patent No.: US 10,425,466 B2
(45) Date of Patent: *Sep. 24, 2019

(54) FLOW CYTOMETER REMOTE MONITORING SYSTEM

(71) Applicant: INGURAN, LLC, Navasota, TX (US)

(72) Inventors: James J. Salinas, College Station, TX (US); Kenneth M. Evans, College Station, TX (US)

(73) Assignee: Inguran, LLC, Navasota, TX (US)

( * ) Notice: Subject to any disclaimer, the term of this patent is extended or adjusted under 35 U.S.C. 154(b) by 840 days.

This patent is subject to a terminal disclaimer.

(21) Appl. No.: 14/176,508

(22) Filed: Feb. 10, 2014

(65) Prior Publication Data

US 2014/0170696 A1 Jun. 19, 2014

Related U.S. Application Data

(63) Continuation of application No. 12/736,684, filed as application No. PCT/US2009/002715 on May 1, 2009, now Pat. No. 8,670,942, which is a continuation-in-part of application No. 12/151,156, filed on May 2, 2008, now Pat. No. 8,060,353.

(51) Int. Cl.
*G01N 33/50* (2006.01)
*H04L 29/08* (2006.01)
*G01N 15/14* (2006.01)
*G01N 35/00* (2006.01)

(52) U.S. Cl.
CPC ......... *H04L 67/06* (2013.01); *G01N 15/1425* (2013.01); *G01N 35/00871* (2013.01); *H04L 67/12* (2013.01); *G01N 15/1459* (2013.01); *G01N 15/1463* (2013.01); *G01N 2015/149* (2013.01); *G05B 2223/06* (2018.08)

(58) Field of Classification Search
None
See application file for complete search history.

(56) References Cited

U.S. PATENT DOCUMENTS

| 5,179,651 | A | 1/1993 | Taaffe et al. |
|---|---|---|---|
| 5,247,372 | A | 9/1993 | Tsutamori et al. |
| 5,442,749 | A | 8/1995 | Northcutt et al. |
| 5,577,190 | A | 11/1996 | Peters |
| 5,764,235 | A | 6/1998 | Hunt et al. |
| 5,778,368 | A | 7/1998 | Hogan et al. |
| 6,006,231 | A | 12/1999 | Popa |
| 6,118,444 | A | 9/2000 | Garmon et al. |
| 6,449,639 | B1 | 9/2002 | Blumberg |
| 6,574,629 | B1 | 6/2003 | Cooke, Jr. et al. |
| 6,631,407 | B1 | 10/2003 | Mukaiyama et al. |
| 6,856,414 | B1 | 2/2005 | Haneda et al. |
| 6,938,211 | B1 | 8/2005 | Chang et al. |
| 7,085,814 | B1 | 8/2006 | Gandhi et al. |
| 7,209,592 | B2 | 4/2007 | Keller et al. |
| 7,215,832 | B1 | 5/2007 | Yamaguchi |
| 7,233,702 | B2 | 6/2007 | Shiraishi |
| 7,236,165 | B2 | 6/2007 | Dautelle |
| 7,259,729 | B2 | 8/2007 | Shastri et al. |
| 7,277,586 | B2 | 10/2007 | Adachi |
| 7,302,118 | B2 | 11/2007 | Liu et al. |
| 7,308,189 | B2 | 12/2007 | Ando et al. |
| 7,317,840 | B2 | 1/2008 | DeCegama |
| 7,319,480 | B2 | 1/2008 | Akiyama et al. |
| 7,321,673 | B2 | 1/2008 | Watai et al. |
| 7,324,695 | B2 | 1/2008 | Krishnan et al. |
| 7,330,878 | B2 | 2/2008 | Slavin et al. |
| 2002/0186212 | A1 | 12/2002 | Matsumoto et al. |
| 2003/0078703 | A1 | 4/2003 | Potts et al. |
| 2006/0010392 | A1 | 1/2006 | Noel et al. |
| 2007/0019876 | A1* | 1/2007 | Cai ........... H04N 19/63 382/240 |
| 2007/0112785 | A1 | 5/2007 | Murphy et al. |
| 2007/0117086 | A1* | 5/2007 | Evans ........... C12N 5/0612 435/4 |
| 2007/0143033 | A1 | 6/2007 | Zhang et al. |
| 2007/0255756 | A1 | 11/2007 | Satomura et al. |
| 2007/0286451 | A1 | 12/2007 | Rhoads |
| 2008/0076470 | A1 | 3/2008 | Ueda et al. |
| 2010/0223556 | A1 | 9/2010 | Wakabayashi et al. |
| 2010/0299278 | A1 | 11/2010 | Kriss et al. |

FOREIGN PATENT DOCUMENTS

| EP | 0620428 A1 | 10/1994 |
|---|---|---|
| JP | 2007-248080 | 9/2007 |
| JP | 4782689 | 7/2011 |

(Continued)

OTHER PUBLICATIONS

Battye, Web Servlet-Assisted, Dial-In Flow Cytometry Data Analysis, Nov. 2000, Cytometry, No. 43, pp. 143-149.*
EP Examination Report dated Feb. 13, 2015 issued in corresponding EP Application No. 090739245.0.
EP Extended Search Report dated May 2, 2014, issued in corresponding EP Application No. 09739245.0 (10 pp).
Battye, F.L., "Web servlet—assisted, dial—in flow cytometry data analysis", Cytometry, vol. 43, Issue 2, pp. 143-149, 2001.
CA Notice of Allowance dated Apr. 22, 2016 issued in corresponding CA Application No. 2,725,423.
CA Office Action dated Apr. 22, 2016 issued in corresponding CA Application No. 2,725,423.
CA Notice of Allowance dated Jul. 24, 2015 issued in corresponding CA Application No. 2,725,423.

(Continued)

*Primary Examiner* — Jason M Sims
(74) *Attorney, Agent, or Firm* — Ryan Christensen; Hashim Rahman

(57) ABSTRACT

Generally, a computer implemented remote monitoring system which generates a viewable reduced byte data representation for each one of a plurality of analyzed instrument signals. Specifically, a flow cytometer remote monitoring system which generates a viewable reduced byte data representation for each one of a plurality analyzed flow cytometer signals.

8 Claims, 9 Drawing Sheets

(56) References Cited

FOREIGN PATENT DOCUMENTS

| WO | 9839728 A1 | 9/1998 |
|---|---|---|
| WO | 2011/159708 A1 | 12/2011 |

OTHER PUBLICATIONS

AR Notice of Allowance dated Jul. 8, 2015 issued in corresponding AR Application No. P20080104850.
Chinese Decision of Grant dated Nov. 14, 2013, issued in corresponding CN Application No. 200980124810.5 (5 pp).
Australian Examination Report dated Feb. 18, 2014, issued in corresponding AU Application No. 2013200479 (2 pp).
U.S. Notice of Allowance dated Dec. 13, 2013, issued in corresponding U.S. Appl. No. 12/736,684 (10 pp).
Australian Notice of Acceptance dated Apr. 9, 2014, issued in corresponding AU Application No. 2013200479 (2pp).
Argentine Office Action dated Aug. 11, 2014, issued in related AR Application No. 20080104850 (4 pp).
Canadian Office Action dated Jun. 27, 2014, issued in related CA Application No. 2,725,423 (3 pp).
Canadian Office Action dated Jul. 26, 2013 issued in corresponding CA Application No. 2725423 (3 pages).
Japanese Office Action dated Jul. 30, 2013 issued in corresponding JP Application No. 2011-507470 (6 pages).
Chinese Second Office Action dated May 16, 2013, (corresponding CN Application No. 200980124810.5) (4 pages).
AU Notice of Acceptance dated Jan. 14, 2013, (corresponding Australian Patent Application No. 2009241769) (3 pages).
JP Office Action dated Oct. 22, 2012, (corresponding Japanese Patent Application No. 2011-507470) (8 pages).
Japanese Laid-Open Publication No. 10-215494 (in Japanese; English Abstract provided) (2 pages).
Japanese Laid-Open Publication No. 2002-372543 (in Japanese; English Abstract provided) (2 pages).
Japanese Laid-Open Publication No. 04-507040. (in Japanese; English WO 9013315 provided) (65 page).
Japanese Laid-Open Publicatin No. 2006-180212. (in Japanese; English Abstract provided) (2 pages).
Japanese National Phase PCT Laid-Open Publication No. 09-509250 (in Japanese; abstract provided) (1 page).
Japanese National Phase PCT Laid-Open Publicaion No. 09-509795 (in Japanese; abstract provided) (1 page).
Chinese First Office Action dated Sep. 5, 2012 issued in corresponding CN Application No. 200980124810.5 (18 pages).
Australian Examination Report No. 1 dated Jun. 23, 2012 issued in corresponding AU Application No. 2009241769 (3 pages).
Australian Examination Report No. 2 dated Aug. 27, 2012 issued in corresponding AU Application No. 2009241769 (3 pages).
International Search Report and Written Opinion dated Jul. 7, 2009 issued in corresponding PCT Application No. PCT/US2009/002715 (11 pages).
PCT International Patent Application No. PCT/US2009/002715, filed May 1, 2009.
U.S. Appl. No. 12/151,156, filed May 2, 2008.
IN Examination Report dated Jan. 1, 2018 issued in related IN Application No. 4099/KOLNP/2010.
CA Examination Report dated Feb. 28, 2019 in related CA Appl. No. 2,964,584.
BR Examination Report dated May 28, 2019 in related BR Appl. No. PI0912002-5.

* cited by examiner

FLOW CYTOMETER REMOTE MONITORING SYSTEM

This application is a continuation of U.S. patent application Ser. No. 12/736,684, filed on Oct. 29, 2010, which is the United States National Stage of International Patent Cooperation Treaty Application No. PCT/US2009/002715, filed May 1, 2009, which is a continuation-in-part of U.S. patent application Ser. No. 12/151,156, filed on May 2, 2008, now U.S. Pat. No. 8,060,353, each of which are incorporated herein by reference.

I. TECHNICAL FIELD

Generally, a computer implemented remote monitoring system which generates a viewable reduced byte data representation for each one of a plurality of analyzed instrument signals. Specifically, a flow cytometer remote monitoring system which generates a viewable reduced byte data representation for each one of a plurality analyzed flow cytometer signals.

II. BACKGROUND

Flow cytometry systems can be utilized to analyze at least one of a plurality of particles. The plurality of particles is typically a population of biological particles such as sperm cells, stem cells, blood cells, bacteria, or the like. The analysis of a population of particles can occur at analysis rates of between about 10,000 particles per second and about 200,000 particles per second depending on the of the population of particles and the manner of analysis. The analysis of individual particles in a population can provide information relating to the presence or absence or the amount of one or more particle characteristics. The relative presence or absence or the amount of one or more particle characteristics may be used to as the basis on which to differentiate individual particles of an analyzed population into two or more discrete subpopulations of particles. The discreet subpopulations of particles can then be separated from the main population of particles and isolated as discrete subpopulations of particles as further described herein.

The operator of the flow cytometer device relies on the use of a viewable data representation to make decisions about the operation of the flow cytometer device. Since the flow cytometer device can be analyzing many hundreds of millions of particles per hour and may be further sorting many millions of cells per hour, the viewable data representation may be designed to show the flow cytometer operator a continuously updated viewable data representation. The continuously updated viewable data representation may include analysis data of a fraction of the population of particles analyzed along with operating parameters for the flow cytometer device updated in discrete analysis intervals. For example, the viewable data representation may be updated every 100 milliseconds, in the form of histograms of the most recent 10 seconds of particle analysis data.

The flow cytometer operator relies on the viewable data representation to both manage and control procedures and parameters for particle analysis and sorting but to also to control the hardware configuration of the flow cytometer device with regard to three dimensional positioning of components such as the fluidic nozzle, beam shaping optics and optical focus for detection, and the like. The flow cytometer operator may also control the rate of droplet formation, the amplitude of the energy used in droplet formation and the voltage applied to droplet streams without use of the viewable data representation; although these types of adjustments can change the scale and precision of measurements being made in analysis of the population of particles and result in changes to the viewable data representation displayed to the flow cytometer operator. Accordingly, the viewable data representation provides a source of real time information utilized by the flow cytometer operator to adjust particle analysis and flow cytometer device parameters.

The viewable data representation generated during operation of the flow cytometer device can be generated in an image format selected by the flow cytometer operator which can be configured by selection of particular data masks and data sets which populate such data masks which are typically provided as histograms. Although the analysis data generated by a flow cytometer device may be collected and stored in a memory element of the flow cytometer device as raw data files, the operation of a flow cytometer device to assess over a duration of time the operating condition, adjust analysis and hardware parameters to optimize the operating condition, or trouble shoot the operating condition for software or hardware problems may require access to a substantial portion or all of the history and detail of the viewable data representation. However, use of a substantial portion of the history and detail the viewable data representation during operation of a flow cytometer device, or other similar analysis device, can present certain problems.

One substantial problem with using a substantial portion of the history and detail of viewable data representation may be competition for computer processing capacity of the flow cytometer device (or other devices which provide similar viewable data representations) resulting in a delay updating display of the viewable data representation which in certain instances can appear as interrupted or non-continuous display of the viewable data representation. In certain instances depending on the flow cytometer device, attempts to access and utilize stored viewable data representations or attempts to control the functionalities of the flow cytometer device remotely can interfere with the normal operation and particle analysis of the flow cytometer device.

Another substantial problem may be that the viewable data representation is stored in files that subtend some user defined amount of detail in screens per second and in seconds per file. These file management and data storage requirements can overload the computer processing unit ("CPU"), read only memory ("RAM"), and the local memory storage capacity of individual flow cytometer devices, especially when such flow cytometer devices are equipped with versions of CPU, RAM, operating systems ("OS"), and other programs that were not designed to operate at speeds required for use of large file sizes associated with viewable data representations in form of images, video, histograms, or similar technology of electronically capturing, recording, processing, storing, transmitting, and reconstructing a sequence of still images.

Another substantial problem may be that viewable data representations in the form of image files and video files, or the like, may be to large to be utilized in the lesser bandwidths of local area networks ("LAN") or virtual private networks ("VPN") to effectively transmit to computers outside of the LAN.

Another substantial problem may be that the effort, time, and cost of providing sufficient storage space in memory for all historical viewable data representation at a level of resolution sufficient to be useful upon retrieval is too great when compared to the value of the viewable data representation stored.

Another substantial problem may be that conventional methods to capture, recording, processing, storing, transmitting, or reconstruct images to provide conventional viewable data representations are not scalable. For example, while conventional methods of providing a viewable data representation may be practical in regard to one flow cytometer device, it may not be possible or practical in the context of providing a viewable data representation for a plurality of flow cytometer devices such as 50 or 100 flow cytometer devices (or even a greater number of devices) at a single location or in a LAN environment, or in a distributed network of flow cytometer devices, or a plurality of distributed LAN environments connected in a wide area network ("WAN") environment.

III. DISCLOSURE OF INVENTION

Accordingly, a broad object of the invention can be to provide an inventive computer implemented data management system to electronically capture, record, process, store, transmit, or reconstruct a sequence of still images generated by the operation of a device.

A second broad object of the invention can be to provide a device which includes the inventive data management system to electronically capture, record, process, store, transmit, or reconstruct a sequence of still images in the form of a viewable reduced byte data representation.

A third broad object of the invention can be to provide a flow cytometer device which includes the inventive data management system to electronically capture, record, process, store, transmit, or reconstruct a sequence of still images generated during operation in the form of a viewable reduced byte data representation.

A fourth broad object of the invention can be to provide a method of using the computer implemented data management system to electronically capture, record, process, store, transmit, or reconstruct a sequence of still images generated by the operation of a device to monitor one or more devices from a remote location.

A fifth broad object of the invention can be to provide method of producing a device which includes the computer implemented data management system to electronically capture, record, process, store, transmit, or reconstruct a sequence of still images generated by the operation of a device to monitor one or more devices from a remote location.

A sixth broad object of the invention can be to provide a method of remote monitoring of each of a plurality of viewable data representations generated by a corresponding plurality of flow cytometers coupled in one or more LAN environments.

Naturally, further objects of the invention are disclosed throughout other areas of the specification, drawings, photographs, and claims.

IV. BRIEF DESCRIPTION OF THE DRAWINGS

V. MODE(S) FOR CARRYING OUT THE INVENTION

Figure 1:
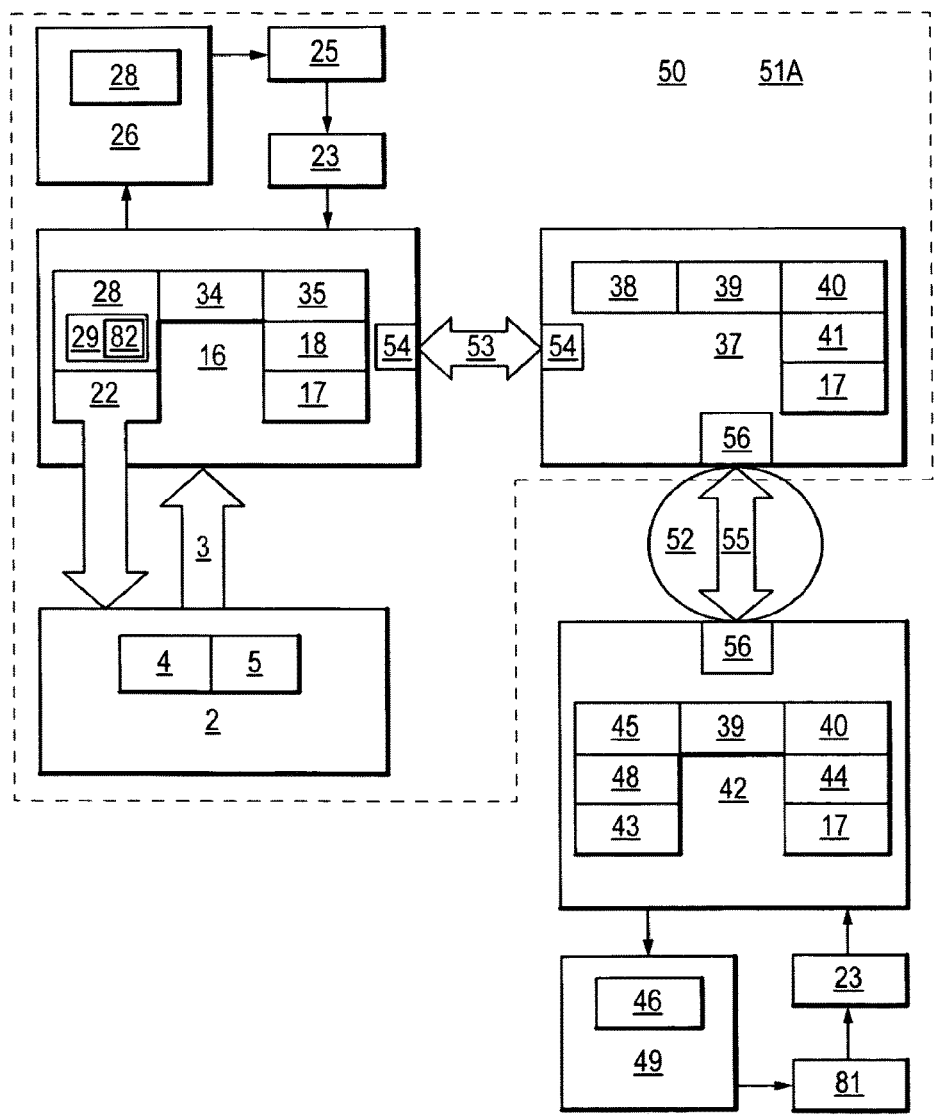
FIG. 1 is a block diagram of hardware means and network means of a particular embodiment of the invention.

Generally, computer implemented remote monitoring system which generates a viewable reduced byte data representation for each one of a plurality of analyzed instrument signals. Specifically, a flow cytometer remote monitoring system which generates a viewable reduced byte data representation for each one of a plurality analyzed flow cytometer signals.

Referring generally to FIGS. 1-9, the inventive instrument or flow cytometer remote monitoring system (1) may be described herein in terms of functional block components, screen shots, and various process steps. It should be appreciated that such functional blocks may be realized by any number of hardware or software components configured to perform the specified functions. For example, the inventive flow cytometer remote monitoring system (1) may employ various integrated circuit components which function without limitation as memory elements, processing elements, logic elements, look-up tables, or the like, which may carry out a variety of functions under the control of one or more microprocessors or other control devices.

Similarly, the software elements of the present invention may be implemented with any programming or scripting language such as C, C++, Java, COBOL, PERL, Labview, or any graphical user interface programming language, extensible markup language (XML), Microsoft's Visual Studio .NET, Visual Basic, or the like, with the various algorithms or Boolean Logic being implemented with any combination of data structures, objects, processes, routines or other programming elements. Further, it should be noted that the present invention might employ any number of conventional wired or wireless techniques for data transmission, signaling, data processing, network control, and the like.

It should be appreciated that the particular implementations shown and described herein are illustrative of the invention and its best mode and are not intended to otherwise limit the scope of the present invention in any way. Indeed, for the sake of brevity, conventional data networking, application development and other functional aspects of the systems (and components of the individual operating components of the systems) may not be described in detail herein. Furthermore, the connecting lines shown in the various Figures contained herein are intended to represent exemplary functional relationships or physical couplings between the various elements. It should be noted that many alternative or additional functional relationships or physical connections may be present in various embodiments of the inventive flow cytometer remote monitoring system (1).

As will be appreciated by one of ordinary skill in the art, the present invention may be embodied as a method of data processing, a data processing system, a device for data processing, a computer program product, or the like. Accordingly, the present invention may take the form of an entirely software embodiment, an entirely hardware embodiment, or an embodiment combining aspects of both software and hardware. Furthermore, the present invention may take the form of a computer program product on a computer-readable storage medium having computer-readable program code means embodied in the storage medium. Any suitable computer-readable storage medium may be utilized, including hard disks, CD-ROM, optical storage devices, magnetic storage devices, ROM, flash RAM, or the like.

The present invention may be described herein with reference to screen shots, block diagrams and flowchart illustrations of the flow cytometer remote monitoring system (1) to describe computer programs, applications, or modules which can be utilized separately or in combination in accordance with various aspects or embodiments of the invention. It will be understood that each functional block of the block diagrams and the flowchart illustrations, and combinations of functional blocks in the block diagrams and flowchart illustrations, respectively, can be implemented by computer program instructions. These computer program instructions may be loaded onto a general purpose computer, special purpose computer or other programmable data processing apparatus to produce a machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware based computer systems which perform the specified functions or steps, or suitable combinations of special purpose hardware and computer instructions.

Furthermore, while embodiments of the inventive flow cytometer remote monitoring system (1) may be described in the context of monitoring a flow cytometer (2), the invention is not so limited, and the data management functionalities and image management functionalities of inventive flow cytometer remote monitoring system (1) can be utilized in the context of monitoring a numerous and wide variety of instruments including but not limited to chromatographs, spectrophotometers, computed topographs, computed tomographs, or the like. The term "flow cytometer" for the purposes of the embodiments of the invention described herein generally means any device configured to count, examine, or sort microscopic particles suspended in a stream of fluid such counting, examination or sorting can be based upon single or multiple parametric analysis of the physical or chemical characteristics of single cells flowing through an optical or electronic detection apparatus. A flow cytometer (2) can as non-limiting examples be configured to provide a single stream of fluid in which particles are entrained for analysis or a plurality of streams of fluid each stream of fluid entraining particles for analysis with particles in each such fluid stream interrogated by one or more laser beams each of which can be emitted by a corresponding one laser device or can be produced by splitting a single laser beam into a plurality of laser beams for interrogation of one fluid stream or a plurality of fluid streams. The signal generated by the optical or electronic detection apparatus for each stream can be processed as single channel of data or multiple channels of data at independent rates using one or a plurality of processors in parallel. A non-limiting example of a flow cytometer (2) device suitable for use in embodiments of the inventive flow cytometer remote monitoring system (1) can be a MOFLO® SX or MOFLO® SX XDP flow cytometer available from Dako Colorado, Inc. or can be flow cytometers available from Icyte, Becton Dickinson, Cytopeia, Partec, or the like; the invention is not so limited. Certain flow cytometer (2) devices can be utilized for FACS flow cytometry for sorting of heterogeneous mixtures of particles; however, the invention is not limited to the utilization of any particular type or kind of a flow cytometer (2) device.

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a viewable data representation" refers to one or more of those viewable data representations. As such, the terms "a" or "an", "one or more" and "at least one" can be used interchangeably herein. Furthermore, the term "selected from the group consisting of" refers to one or more of elements in the list that follows, including combinations of two or more of the elements.

First referring primarily to FIG. 1, a block diagram provides a general overview of elements (each element further described below) which can be used to implement a particular non-limiting embodiment of the inventive flow cytometer remote monitoring system (1). A first computer user (25) can through use of a command input device (23) such as keystroke of a computer keyboard or a mouse send commands to the processing unit (17) of a first computer (16) to deliver computer operating instructions to a flow cytometer (2) (or other type of computer controlled device or instrument). The flow cytometer (2) can generate a signal (3) which varies based upon the amount of at least one particle characteristic (4) of a plurality of particles (5). The signal (3) can be analyzed by the first computer (16) which can further function to generate a viewable data representation (28) of the analyzed signal which can be viewed by the first computer user (25) on a first computer monitor (26).

For the purposes of this invention the term "viewable data representation" means an intermittently updated graphical display of data generated by a device viewable by a computer user (25), including, as non-limiting examples, chromatograms, computed tomographies, histograms or the like. As a specific non-limiting example, see FIG. 8 which shows a viewable data representation (28) generated having the form of a histogram (29) showing the separation of a plurality of sperm cells (9) into X chromosome bearing sperm cells (14) and Y chromosome bearing sperm cells (15).

The first computer user (25) can view the viewable data representation (28) to understand the functional condition of the flow cytometer (2) (or other device or instrument). The first computer (16) can further function to generate a plurality of time bound data representation files (35) of the viewable data representation (28) which can be temporarily stored in a memory element (18) of the first computer (16).

A second computer (37) can provide an image processor (38) which functions to convert the temporary copies of the plurality of time bound data representation files (35) into a first plurality of reduced byte data representation files (39) and a second plurality of reduced byte data representation files (40) retrievably stored in the second computer memory element (41). The second computer (37) as part of a LAN (50) can upon request serve all or part of the first plurality of reduced byte data representation files (39) or the second plurality of reduced byte data representation files (40) to a third computer (42) over a WAN (52).

Figure 2:
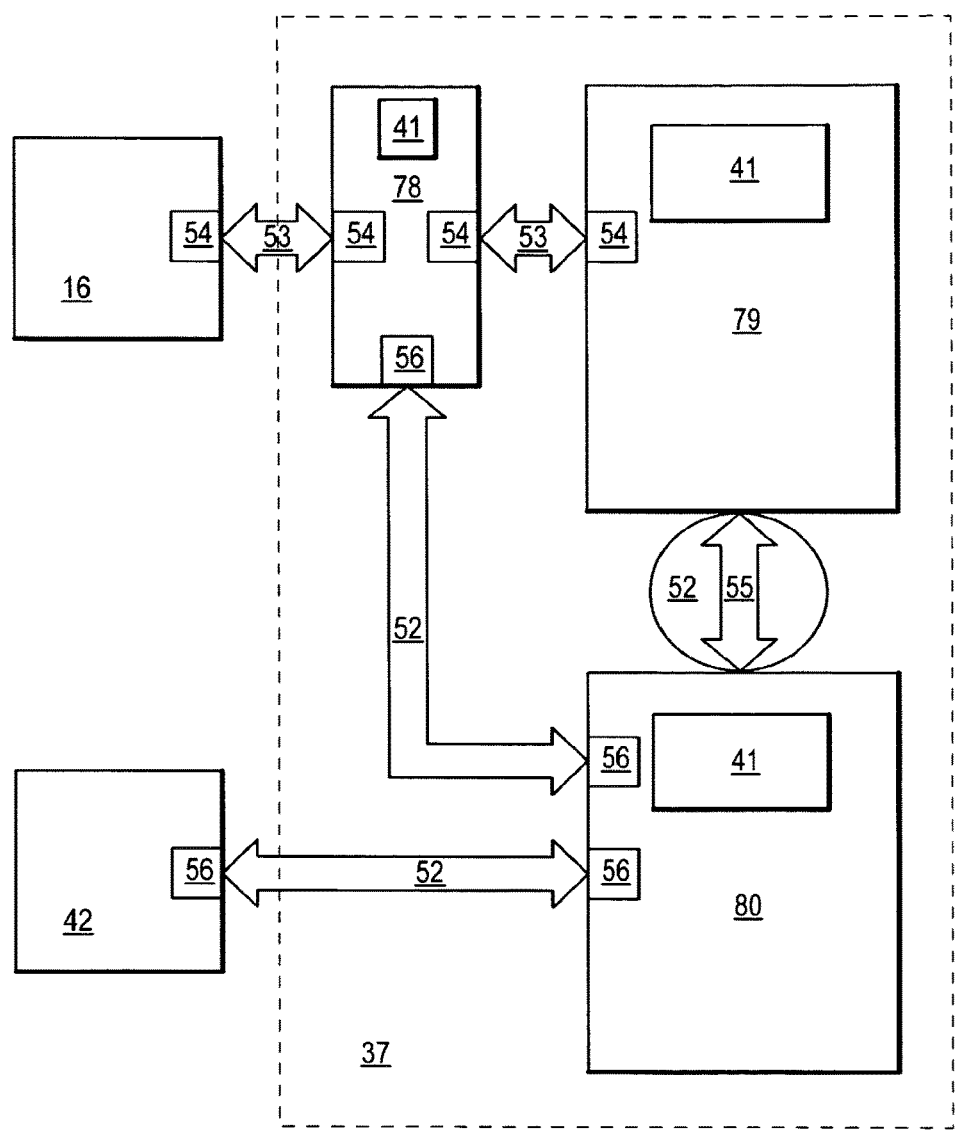
FIG. 2 is a block diagram of hardware means and network means of another particular embodiment of the invention.

Now referring specifically to FIG. 2, which provides a particular example of the general hardware means and network means of the second computer (37) including a LAN file server (78) dedicated to provide the functions of converting the temporary copies of the plurality of time bound data representation files (35) into a first plurality of reduced byte data representation files (39) and a second plurality of reduced byte data representation files (40) retrievably stored in the second computer memory element (41) for a flow cytometer or a plurality of flow cytometers in a LAN environment. The embodiment can further provide a second local file server (79) which supports other processing functions in the LAN environment. The embodiment can further provide a WAN file server (80) which further supports the functions of the a LAN file server (78) of converting the temporary copies of the plurality of time bound data representation files (35) into a first plurality of reduced byte data representation files (39) and a second plurality of reduced byte data representation files (40) retrievably stored in the second computer memory element (41) for a flow cytometer or a plurality of flow cytometers in the LAN environment.

Again referring primarily to FIG. 1, a third computer user (81) operating the third computer (42) can generate a request to receive all or part of the first plurality of reduced byte data representation files (39) or the second plurality of reduced byte data representation files (40) retrievably stored in the second computer memory element (41) of any one of a plurality of LANs (50). The files can be transferred from the second computer (37) utilizing a WAN communications device (56) over WAN logical connections (55). An image generator (45) provided by the third computer (42) can generate a viewable reduced byte data representation (46) of all or part of the first plurality of reduced byte data representation files (39) or the second plurality of reduced byte data representation files (40) transferred from the second computer (37) which can be displayed on a third computer monitor (49) (for example see FIG. 9 which shows the viewable reduced byte data representation (46) generated from a corresponding two of the plurality of reduced byte data representation files (39) or the second plurality of reduced byte data representation files (40) retrievably stored in the second computer memory element (41) of any one or more of a plurality of LANs (50)) in the form of a histogram showing the separation of sperm cells into X chromosome bearing and Y chromosome bearing populations).

Figure 3:
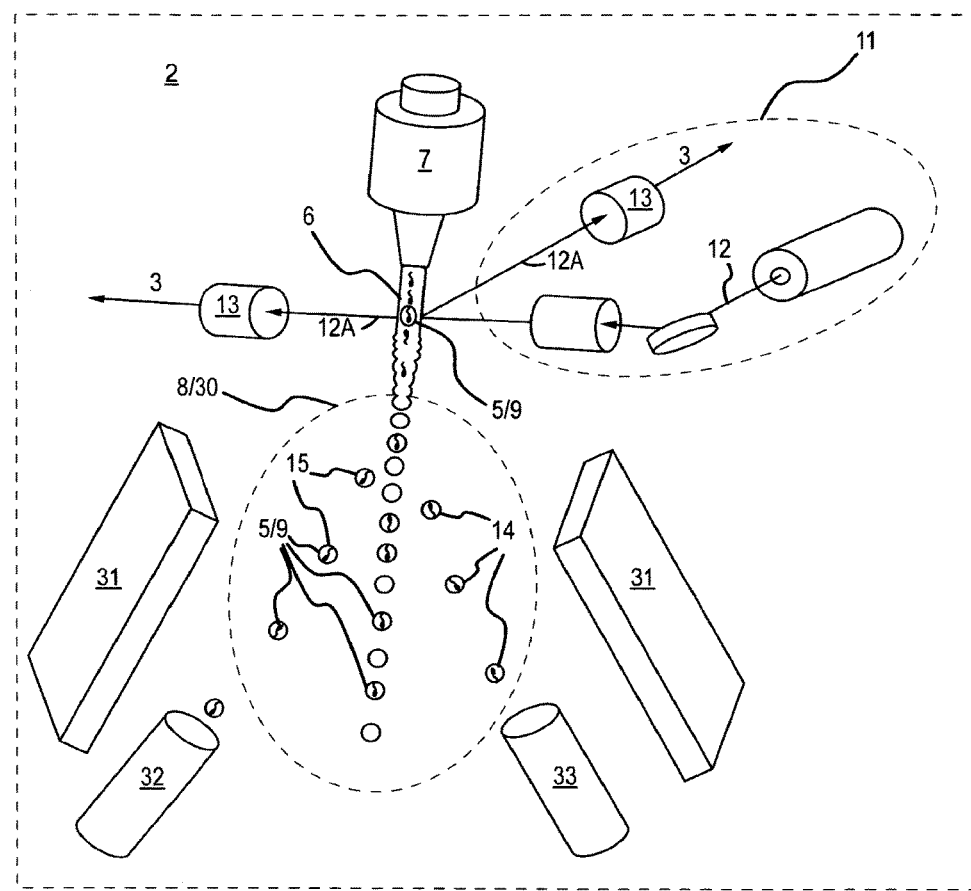
FIG. 3 is a block diagram of a particular device for the analysis and sorting of a plurality of particles.
Figure 3A:
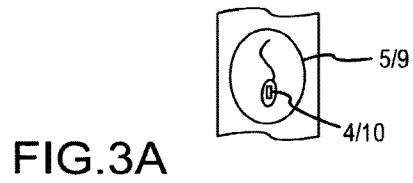
FIG. 3A is broken out portion of a fluid stream in the particular device for analysis and sorting of a plurality of particles.

Now referring primarily to FIGS. 1 and 3, certain embodiments of the inventive flow cytometer remote monitoring system (1) can in part include a flow cytometer (2). The flow cytometer (2) can function to produce a signal (3) (whether analog, analog converted to digital, or digital) which varies whether in frequency, amplitude, or both frequency and amplitude) based upon change in at least one particle characteristic (4) among a plurality of particles (5). The plurality of particles (5) can be biological particles such as cells, sperm cells, organelles, chromosomes, deoxyribonucleic acids (DNA), ribonucleic acids (RNA), DNA fragments, RNA fragments, proteins, protein fragments, peptides, oligonucleotides, or the like, but can also include non-biological particles such as beads, styrene beads, or the like, or as mixtures of biological particles, mixtures of non-biological particles, or mixtures of biological and non-biological particles. The term "at least one particle characteristic" for the purposes of this invention means at least one part, component, or differentially modified part or component common to at least a portion of the plurality of particles (5) entrained in the fluid stream (6) which varies in kind or amount between the plurality of particles (5).

As one non-limiting example, the plurality of particles (5) can be a plurality of sperm cells (9) and the at least one particle characteristic (4) can be the amount of deoxyribonucleic acid ("DNA") (10) contained in each of the plurality of sperm cells (9). The amount of DNA (10) can vary based upon whether the particular one of the plurality of sperm cells (9) contains an X chromosome or a Y chromosome. The X chromosome contains a greater amount of DNA (10) than the corresponding Y chromosome regardless of the male mammal from which the plurality of sperm cells (9) is obtained. Sperm cells (9) can be obtained from any male mammal including for example, a bovid, an ovis, an equid, a pig, a cervid, a canid, a felid, a rodent, a whale, a rabbit, an elephant, a rhinoceros, a primate, or the like, as well as from certain male non-mammal species.

Certain kinds of flow cytometer (2) devices operate to entrain each of the plurality of particles (5) in a fluid stream (6) which exits a nozzle (7) oscillated to produce droplets (8) in the fluid stream (6). Prior to the break off point for each of the droplets (8) each of the plurality of particles (5) in the fluid stream (6) passes through an interrogation means (11) to generate interrogation event rates of between about 10,000 per second and about 200,000 per second. Typically, the interrogation means (11) includes one or more laser beams (12) through which each of the plurality of particles (5) fall. Each interrogated one of the plurality of particles (5) can in response to interrogation by the laser beam(s) absorb or emit an amount of light (12A). For example, DNA can be quantitatively stained with a dye or fluorochrome such as Hoechst 33342. The stained DNA can emit an amount of light (12) in response to being interrogated with a laser beam. X chromosome bearing sperm cells (14) typically emit a greater amount of light (12A) than Y chromosome bearing sperm cells (15) because each X chromosome bearing sperm cell (14) contains a greater amount of stained DNA than a Y chromosome bearing sperm cell (15).

The amount of light (12A) emitted from the interrogated one of the plurality of particles (5) can be received by a photomultiplier element (13). The photomultiplier element (13) converts the received amount of emitted light (12A) into a signal (3) which correspondingly varies based upon change in the amount of emitted light (12A). In the analysis of a plurality of sperm cells (9) with a flow cytometer (2), the signal (3) generated can vary based upon the difference in the amount of light (12) generated by X chromosome bearing sperm cells (14) and Y chromosome bearing sperm cells (15) when passed through the interrogation means (11).

Figure 4:
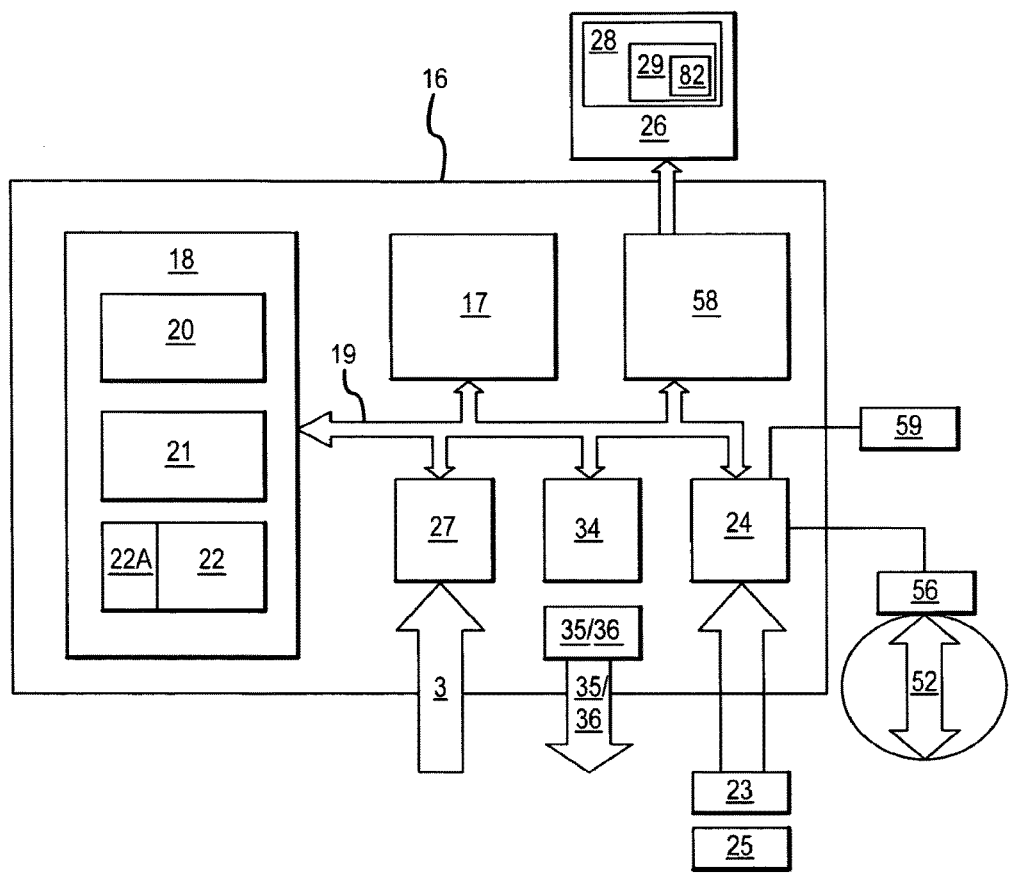
FIG. 4 is a block diagram of hardware means which can be utilized in a particular embodiment of the invention.

Now referring primarily to FIGS. 1, 2 and 4, the flow cytometer (2) (or other instrument) can be coupled to, integral with, or provide a first computer (16) having a processing unit (17), a memory element (18), and a bus (19) which operably couples components of the first computer (16), including, without limitation the memory element (18) to the processing unit (17). The first computer (16) may be a conventional computer, a distributed computer, or any other type of computer capable of delivering instructions to a flow cytometer controller (or other instrument controller) which functions to operate the flow cytometer (or other instrument); the invention is not so limited. The processing unit (17) can comprise without limitation one central-processing unit (CPU), or a plurality of processing units which operate in parallel to process digital information, or a digital signal processor (DSP) plus a host processor, or the like. The bus (19) can be without limitation any of several types of bus configurations such as a memory bus or memory controller, a peripheral bus, and a local bus using any of a variety of bus architectures. The memory element (18) can without limitation be a read only memory (ROM), or a random access memory (RAM), or both. A basic input/output system (BIOS) (20), containing routines that assist transfer of data between the components of the first computer (16), for example during start-up, can be stored in ROM. The first computer (16) can further include a hard disk drive for reading from and writing to a hard disk a magnetic disk drive for reading from or writing to a removable magnetic disk, an optical disk drive for reading from or writing to a removable optical disk such as a CD ROM, or other optical media.

The hard disk drive, magnetic disk drive, and optical disk drive can be connected to the bus (19) by a hard disk drive interface, a magnetic disk drive interface, and an optical disk drive interface, respectively. The drives and their associated computer-readable media provide nonvolatile storage of computer-readable instructions, data structures, program modules and other data of the first computer (16). It can be appreciated by those skilled in the art that any type of computer-readable media that can store data that is accessible by the first computer (16), such as magnetic cassettes, flash memory cards, digital video disks, Bernoulli cartridges, random access memories (RAMs), read only memories (ROMs), and the like, may be provided by a first computer (16) used in embodiments of the inventive flow cytometer remote monitoring system (1).

The first computer (16) can further include an operating system (21) and a flow cytometer controller and particle analysis application (22) which may be stored on or in the hard disk, magnetic disk, optical disk, ROM, in RAM by a particular embodiment of a first computer (16) or alternately the functionalities of the a flow cytometer controller and particle analysis application (22) may be implemented as an application specific integrated chip (ASIC) or file programmable gate array (FPGA), or the like, or combinations or permutations thereof.

A first computer user (25) can enter commands and information into the first computer (16) through one or more command input device(s) (23) such as a keyboard and pointing device such as a mouse. Other command input devices (23) can include a microphone, joystick, game pad, scanner, or the like. These and other command input device(s) (23) are often connected to the processing unit (17) through a serial port interface (24) that can be coupled to the bus (19), but may be connected by other interfaces, such as a parallel port, game port, or a universal serial bus (USB). A monitor (26) or other type of display device can also be connected to the bus (19) via interfaces such as a video adapter (58), or the like. In addition to the monitor (24), the first computer (16) can further include other peripheral output devices (59), such as speakers and printers.

A click event occurs when the first computer user (25) (or other computer user) activates or operates at least one function of the flow cytometer controller and particle analysis application (22), or other program or other application function, through the use of a command which for example can include pressing or releasing the left mouse button while a pointer is located over a control icon displayed on the monitor (26). However, it is not intended that a "click event" be limited to the press and release of the left button on a mouse while a pointer is located over a control icon. Rather, the term "click event" for the purposes of this invention broadly encompasses any manner of command by the first computer user (25) through which a function of the operating system (21) or the flow cytometer controller and particle analysis application (22) is activated or performed, whether through clickable selection of one or a plurality of control icon(s), voice command, keyboard stroke(s), mouse button, touch screen, touch pad, or otherwise.

Again referring primarily to FIGS. 1, 2 and 4, the first computer (16) and the flow cytometer controller and particle analysis application (22) can in part function to provide a signal analyzer (27) which intermittently or continuously converts the signal (3) produced by the flow cytometer (2) into a viewable data representation (28) of change in the at least one particle characteristic (4) of the plurality of particles (5) analyzed. The viewable data representation (28) can be continuously or intermittently displayed on the monitor (26) or updated upon elapse of a short interval of time such as 100 milliseconds. As a non-limiting example, the signal analyzer (27) coupled to a flow cytometer (2) which interrogates a plurality of sperm cells (9) in a corresponding plurality of droplets (8) can generate a viewable data representation (28) in the form of a histogram (29) which varies based on a frequency of Y chromosome bearing sperm cells (14) or a frequency of X chromosome bearing sperm cells (15) identified within the plurality of sperm cells (9). Certain embodiments of the signal analyzer (27) can further function to establish parameters and timed events by which the plurality of particles (5) can be separated, parsed or divided based upon the presence, absence, or amount of the at least one particle characteristic (4).

As a non-limiting example, a flow cytometer (2) such as a MOFLO® SX can used to separate or sort the plurality of particles (5) into, discreet sub-populations based upon at least one particle characteristic (4). Subsequent to exiting the nozzle (7), the fluid stream (6) can break into droplets (8) each of which can contain a corresponding one each of the plurality of particles (5). Based on the above-described analysis of each of the plurality of particles (5) in the fluid stream (6), the droplets can be differentiated based on at least one particle characteristic (4) and separated by applying a charge (whether positive or negative) to each one of the droplets (8) analyzed and then deflecting the trajectory of each of the droplets (8) by passing the droplets (8) through a pair of charged plates (31). The trajectory of the positively charged droplets can be altered for delivery to a first container (32) and the trajectory of the negatively charged droplets can be altered for delivery to a second container (33). Uncharged droplets are not deflected and can be delivered to a third container (34) or to a waste stream. With respect to the separation of a plurality of sperm cells (10), a plurality of particle populations (30) can include X chromosome bearing sperm cells (14) isolated in the first container (32) and Y chromosome bearing sperm cells (15) isolated in the second container (33).

Again referring primarily to FIG. 4, the first computer (16) can further provide an image representation generator (34) which can generate one or a plurality of time bound data representation files (35) of the viewable data representation (28) of change in at least one particle characteristic (4) of the plurality of analyzed particles (5) without generating an amount of lag in displaying the viewable data representation (28) or in the operation of functionalities of the flow cytometer (2). The term "lag" for the purposes of this invention means a reduction in performance or a delay in the generation of the viewable data representation (28) or a delay in a function of the flow cytometer (or other instrument) due to competition by various portions of the operating system (21) or the flow cytometer controller and particle analysis application (22) or other program or application for support by the a processing unit (17).

Typically, the plurality of time bound data representation files (35) of the viewable data representation (28) will include a plurality of bit map image representations (36) or screen shots of the viewable data representation (28) of change in at least one particle characteristic (4) of the plurality of analyzed particles (5) intermittently generated at a pre-determine rate. The pre-determined rate at which each of the plurality of time bound data representation files (35) can be generated will typically be variably adjustable between about 0.1 seconds and about 5 seconds, although other lesser or greater pre-determined rates can be selected so long as the rate does not generate a lag in analyzing the signal (3) generated by the flow cytometer (2) or the function of the flow cytometer (2). The time bound data representation files (35) can be stored temporarily in the memory element (18) of the first computer (16). Typically, each of the plurality of time bound data representation files (35) (generally as a plurality of bit map representations (36)) comprise a file of between about three megabytes and about six megabytes, although the invention is not so limited and each file can include a lesser or greater number of bytes.

Certain embodiments of the first computer (16) provided with a flow cytometer (2) (or other analysis device) may not provide the functionalities required to capture or generate the plurality of time bound data representation files (35) above-described. In that case a time bound data representation file generator (22A) in the form of a small software application can stored in the memory element (18) and can function to periodically capture the viewable data representation (28) as above-described to provide the time bound data representation files (35) which can be transferred to the second computer (37).

Figure 5:
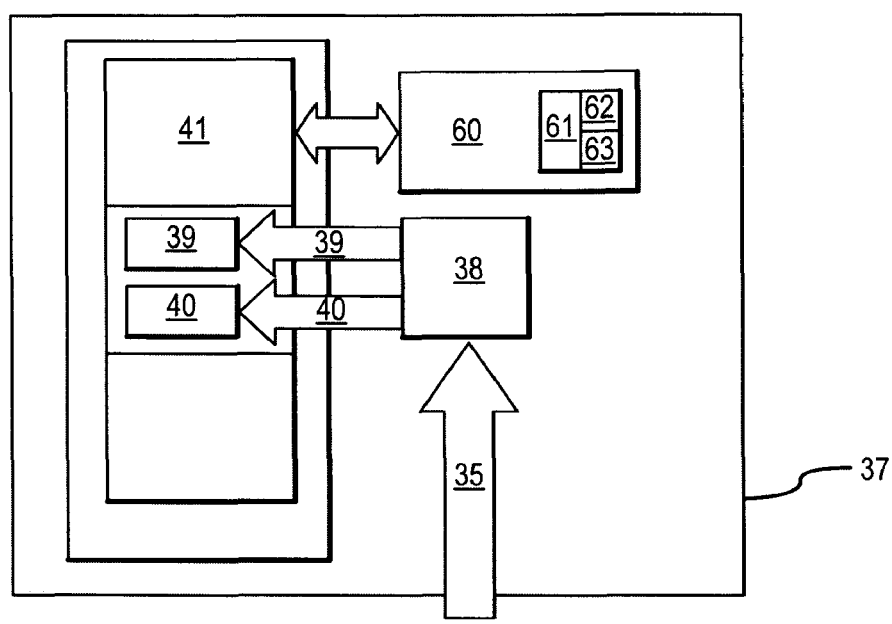
FIG. 5 is block diagram of hardware means which can be utilized in a particular embodiment of the invention.

Now referring primarily to FIG. 5, the inventive flow cytometer remote monitoring system (1) can further include a second computer (37) linked to the first computer (16). The second computer (37) can provide the same or similar hardware means and software means as the first computer (16) although only a memory element (41) is shown along with sufficient hardware means and software means which function to provide an image processor (38). The image processor (38) can function to generate a first plurality of reduced byte data representation files (39) which correspond to each of the plurality of time bound data representation files (35) served from the first computer (16) upon request by the second computer (37). For the purposes of this invention the term "a reduced byte data representation files" (39) comprises an image file of a lesser bytes than the corresponding time bound data representation file. Typically, each of the plurality of reduced byte data representation files will comprise between about one hundred kilobytes and about two hundred kilobytes (although the invention is not so limited and each file can include a lesser or greater number of bytes). As one example the reduced byte data representation file (39) can be in the form of a .jpeg, which includes substantially lesser bytes than for example a Windows Bitmap format which can be one form of the plurality of time bound image representation files (35) transferred from the first computer (16) to the second computer (37).

The image processor (38) can further function to generate a second plurality of reduced byte data representation files (40) of the plurality of time bound data representation files (35) served from the first computer (16) upon request by the second computer (37) each one having fewer bytes than the corresponding one of said first plurality of reduced byte data representation files (39). The second plurality of reduced byte data representation files (40) each one having fewer bytes than the corresponding one of the first plurality of reduced byte data representation files (39) can each provide as one non-limiting example an image file of between about two kilobytes and about four kilobytes (although the invention is not so limited and each file can include a lesser or greater number of bytes). Again, as one example the image file can be in the form of a .jpeg.

The first plurality of reduced byte data representation files (39) and the second plurality of reduced byte data representation files (40) can be generated in parallel from the corresponding plurality of time bound data representation files (35) or the second plurality of reduced byte data representation files (40) can be produced from the corresponding plurality of first plurality of reduced byte data representation files (39). Each of the first plurality of reduced byte data representation files (39) and the second plurality of reduced byte data representation files (40) can be retrievably stored in the second computer memory element (41) of the second computer (37).

Figure 8:
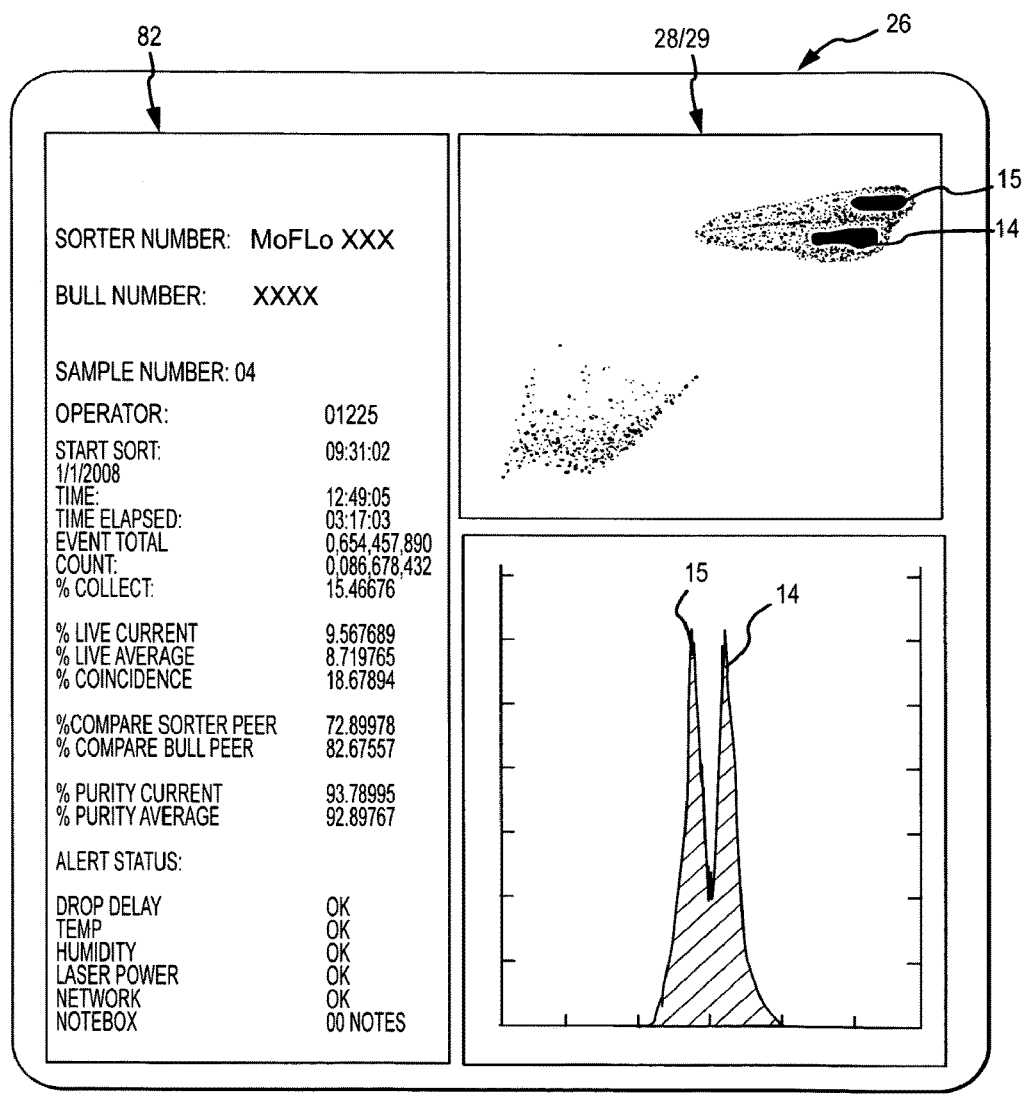
FIG. 8 is a diagram of a viewable data representation generated by a particular embodiment of the invention which includes a flow cytometer.
Figure 9:
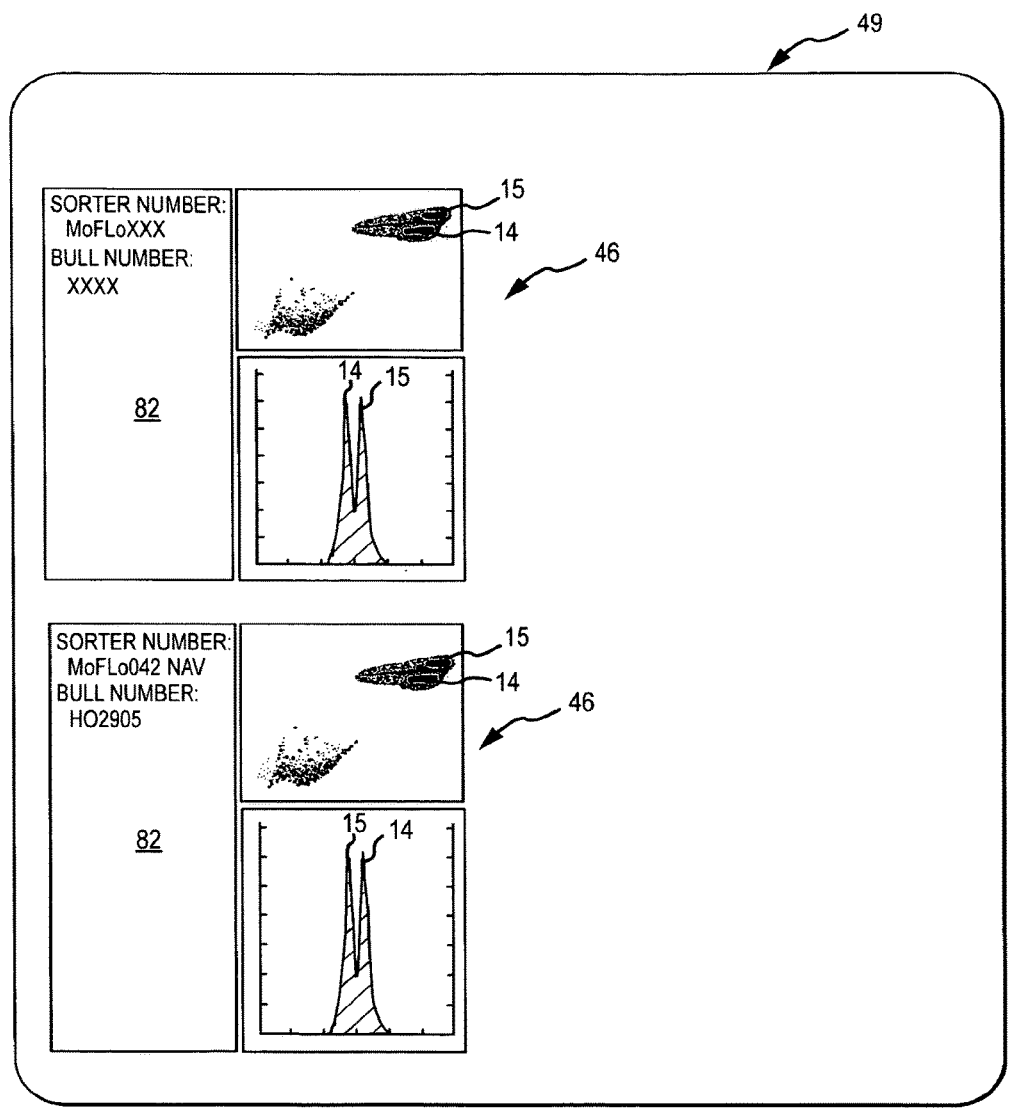
FIG. 9 is a diagram of a plurality of viewable reduced byte data representations generated by a particular embodiment of the invention remotely monitoring a plurality of flow cytometers.

Now referring primarily to FIG. 8, the viewable data representation (28) generated by the flow cytometer particle analysis application (22) of the flow cytometer (2) (or other particle analysis application of another type of device) can further include viewable parametric data elements (82) of numeric data type. As a non-limiting example, in the context of a viewable data representation (28) generated by an embodiment of the flow cytometer particle analysis application (22) for a flow cytometer (2), the viewable parametric data elements (82) can include one or more of sample number, operator identification number, date, drop delay status, temperature status, humidity status, laser power status, network status, particle analysis start time, particle analysis stop time, time elapsed, event rate, total events, particle count, percent particles collected, percent particles aborted, percent particles coincident, or the like. In the context, in which the plurality of particles (5) analyzed are a plurality of sperm cells (9), the viewable parametric data elements (82) can further include current percent live, average percent live, current percent dead, average percent dead, current percent purity, average percent purity, percent compare sorter peer, percent, percent compare bull peer, or the like. The viewable parametric data elements (82) included in the viewable data representation (28) can be converted by the image processor (38) as part of the viewable data representation (28) into a part of a corresponding one of the plurality of time bound data representation files (35) as above described and then converted to a corresponding one of the first plurality of reduced byte data representation files (39) and the second plurality of reduced byte data representation files (40), as above described.

Figure 6:
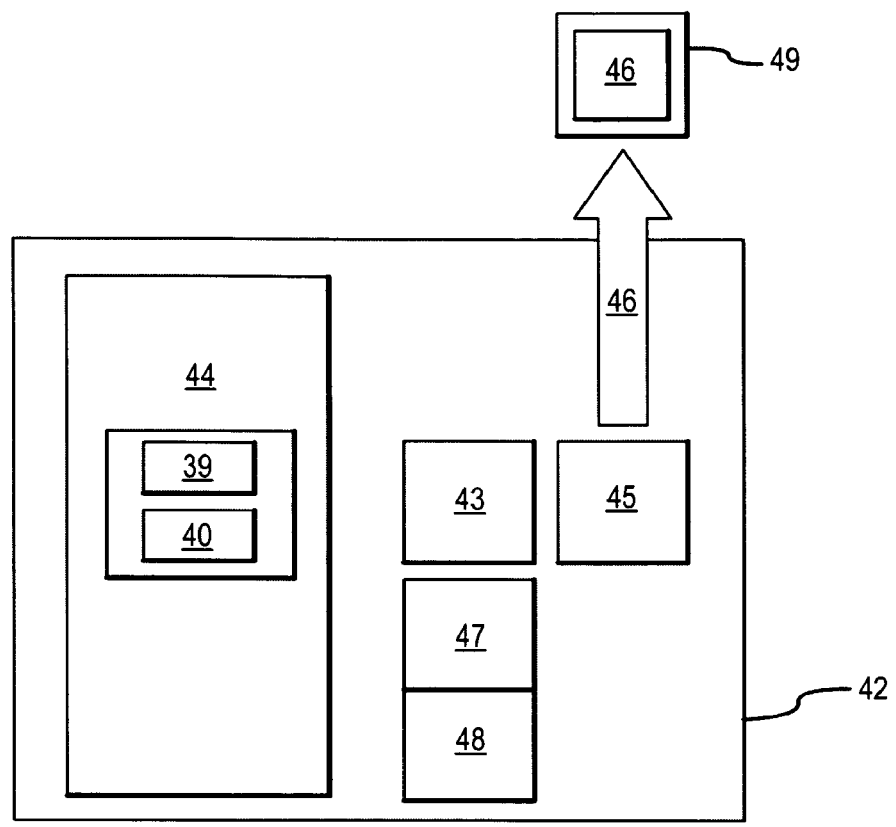
FIG. 6 is block diagram of hardware means which can be utilized in a particular embodiment of the invention.

Now referring to FIG. 6, the inventive flow cytometer remote monitoring system (1) can further include a third computer (42). The third computer (42) can provide the same or similar hardware means and software means as the first computer (16) or sufficient hardware means and software means to function to provide a reduced byte data representation file selection element (43) which can function to generate a request for a selected portion of the first plurality of reduced byte data representation files (39) or a selected portion of the second plurality of reduced byte data representation files (40) to the second computer (37) (the term selected portion can include one or all of the first or second plurality of reduced byte data representation files (39) (40)). The selected portion of the first plurality of reduced byte data representation files (39) or a selected portion of the second plurality of reduced byte data representation files (40) can be stored in a third computer memory element (44). The third computer (42) can further provide an image generator (45) which functions to display the selected portion of the first plurality of reduced by data representation files (39) or the second plurality of reduced byte data representation files (40), or both, in serial order to provide a viewable reduced byte data representation (46) of change in the at least one particle characteristic (4) of said plurality of analyzed particles (5). The a reduced byte data representation file selection element (43) can further include a time period selection element (47) which allows selection of a time bound portion of the first or the second plurality of reduced byte data representation files (39) (40) generated between a first time point and a second time point of the viewable data representation (28).

The image generator (45) of the third computer (42) can further include a viewing rate selector (48) which can function to allow variably adjusted selection of a viewing rate at which to view the viewable reduced byte data representation (46) of change in the at least one particle characteristic (4) of said plurality of analyzed particles (5). As to certain embodiments of the image generator (45) the viewing rate selector (48) allows variably adjustable selection of an accelerated rate at which the viewable reduced byte data representation (46) of change in said at least one particle characteristic of said plurality of particles (5) analyzed can be serially displayed on a third computer monitor (49). As to certain embodiments of the image generator (45) the viewing rate selector (48) allows variably adjustable selection of a decelerated rate at which the viewable reduced byte data representation (46) of change in said at least one particle characteristic of said plurality of analyzed particles can be serially displayed on the third computer monitor (49).

Now referring primarily to FIG. 1, certain embodiments of the inventive flow cytometer remote monitoring system (1) can further include a local area network (50) ("LAN") at a first location (51) which includes local area network logical connections (53) between the flow cytometer (2) and the first computer (16) (or a plurality of flow cytometers (2) each coupled to a corresponding plurality of first computers (16)) and the second computer (37). These logical connections (53) can be achieved by a local area network communication device (54) coupled to or a part of the first computer (16) or the second computer (37) or both. As to certain embodiments of the invention there can be a plurality of local area networks (50) each established at a plurality of discrete locations (51A).

Again referring primarily to FIG. 1, certain embodiments of the inventive flow cytometer remote monitoring system (1) can further include a wide area network (52) ("WAN") such as the Internet which includes wide area network logical connections (55) which allows communication between the third computer (42) established at a second location (56) discrete from the local area network (50) at the first location (51) or the plurality of first locations (51A) and the second computer (37) of any local area network (50). This configuration allows the third computer (42) to retrieve from any second computer (42) any one, a portion of, or all of the plurality of time bound data representation files (35), the a plurality of bit map image representations (36), the first plurality of reduced byte data representation files (39), or the second plurality of reduced byte data representation files (40) from the second computer memory element (41) for display and viewing as above described without generating an amount of lag in analyzing the signal (3) from the at least one flow cytometer (2) by the first computer (16).

When included in a WAN (52), the second computer (37) and the third computer (42) can further include a wide area network communications device (56) such as a modem for establishing communications over the WAN (52) (such as the Internet (57)). The wide area network communications device (56) can be internal or external to the second computer (37) and the third computer (42) and can be connected to the bus (19) via a serial port interface (24). In a WAN (52) environment, the second computer memory element (41) can comprise a plurality of second computer memory elements (41) coupled to the second computer (37) via the WAN which allows distributed retrievable storage of any one, a portion of, or all of the plurality of time bound data representation files (35), the a plurality of bit map image representations (36), the first plurality of reduced byte data representation files (39), or the second plurality of reduced byte data representation files (40). It can be appreciated that the LAN communication device (54), the WAN communications device (56), the LAN logical connections (53), and the WAN logical connections (55) and shown and described are exemplary and other hardware means or logical connection means, and communication means can be utilized for establishing a communications link between the second computer (16) and the third computer (42).

As but one non-limiting example of providing WAN connectivity between any second computer (37) and any third computer (42) for the purposes above-described a pc-engines WRAP1E circuit boards can run Valemount Networks StarOS router software on a 32 meg Compact Flash (CF) memory card to provide a Virtual Distribution System (VDS) tunnel (similar to a Virtual Private Network or VPN) connected to a central router server and each second computer (37) local area network connects as a client to the main central station server to manage all network routing and class based queueing for the entire WAN.

While the computer means and the network means shown in FIGS. 1-6 can be utilized to practice the invention including the best mode, it is not intended that the description of the best mode of the invention or any preferred embodiment of the invention be limiting with respect to the utilization of a wide variety of similar, different, or equivalent computer means or network means to practice embodiments of the invention which include without limitation hand-held devices, such as personal digital assistants or camera/cell phone, multiprocessor systems, microprocessor-based or programmable consumer electronics, network PCs, minicomputers, mainframe computers, PLCs, or the like, in various permutations and combinations.

Figure 7:
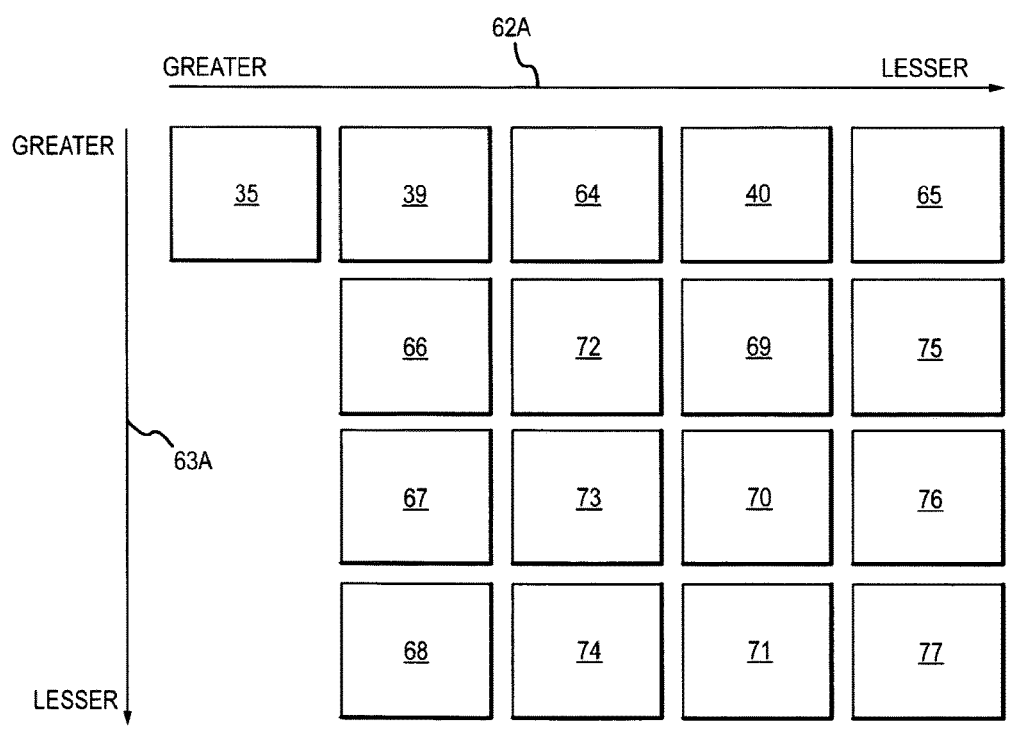
FIG. 7 is a block diagram which shows a particular method of archiving reduced byte data representations generated by a particular embodiment of the invention.

Now referring primarily to FIGS. 5 and 7, the second computer (37) can further include an image archive management module (60) which functions to delete, modify, or otherwise reduce file size of the plurality of time bound data representation files (35), the first plurality of reduced byte data representation files (39), or the second plurality of reduced byte data representation files (40) whether individually or collectively to minimize the memory space in which image files are retrievably stored in the second computer memory element (41). Each one of the plurality of time bound data representation files (35) can be converted into a corresponding one of the first plurality of reduced byte data representation files (39) and a corresponding one of the second plurality of reduced byte data representation files (40). Each one of the second plurality of reduced byte data representation files (40) can be stored in the second computer memory (41) in the LAN (51) until requested by the third computer (42) and each one of the first plurality of reduced byte data representation files (39) can also be stored in the second computer memory (41) until requested by the third computer (42) or until modified or deleted by function of a data storage minimization application (61) which governs image resolution priority (62) and further functions to govern image time value priority (63).

Now referring primarily to FIG. 7, which provides a graph which plots image resolution priority (62A) against image time value priority (63A) with respect to each one of the first plurality of reduced byte data representation files (39) and each one of the second plurality of reduced byte data representation files (40). As can be understood from the Figure, each of the first plurality of reduced byte data representation files (39) can be correspondingly converted into a first plurality of reduced resolution reduced byte data representation files (64) and each of the second plurality of reduced byte data representation files (40) can be correspondingly converted into a second plurality of reduced resolution reduced byte data representation file (65). Additionally, any one of the first plurality of reduced byte data representation files (39), any one of the second plurality of reduced byte data representation files (40), any one of the first plurality of reduced resolution reduced byte data representation files (64), and any one of the second plurality of reduced resolution reduced byte data representation file (65) can reproduced at different times, and then progressively categorized as image time values (66, 67, and 68; 72, 73, and 74; 69, 70, and 71; and 75, 76, and 77 respectively) assigned lesser image time value priority (63A) with elapsed time. In this case, images with greater image time value priority (63A) (for example 66, 72, 69, and 75) can be categorically more important than images with lesser image time value priority (63A) (for example 68, 74, 71, and 77). Similarly, any one of the of the first plurality of reduced byte data representation files (39), any one of the second plurality of reduced byte data representation files (40), and any one of the categories having lesser image value priority (63A) can be progressively rewritten as images of lesser image resolution value priority (62A) and then progressively categorized as image resolution values (72, 75, 73, 76, 74 and 77) assigned lesser image resolution value priority (62A) with decreased resolution.

The number of image value categories (82) could be unlimited but will generally be less than one dozen. Generally, categories with lesser image time value priority (63A) (for example 68, 74, 71, and 77) or lesser image resolution value priority (62A), or both lesser image time value priority (63A) and lesser image resolution value priority (63A) (for example 74 or 77) can be stored on low cost WAN file server (80) (see FIG. 2 for example) while files of greater image time value (for example 66, 72, 69, and 75), can be stored in the second computer memory element (41) of a dedicated LAN file server (78) or general purpose LAN file server (79) (see FIG. 2 for example). Simultaneous deletion and rewriting of image files can occur by function of the data storage minimization application (61) to produce the image value categories (82).

As can be easily understood from the foregoing, the basic concepts of the inventive flow cytometer remote monitoring system (1) may be embodied in a variety of ways. As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "monitor" should be understood to encompass disclosure of the act of "monitoring"—whether explicitly discussed or not—and, conversely, were there effectively disclosure of the act of "monitoring", such a disclosure should be understood to encompass disclosure of a "monitor" and even a "means for monitoring." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the remote monitoring device herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method of remotely monitoring a flow cytometer coupled to a first computer, where the first computer produces a plurality of images as time bound data representation files based on signals generated in the flow cytometer and which are representative of the functional condition of the flow cytometer, the first computer being in communication with a second computer that converts the plurality of time bound data representation files into reduced byte data representation files with an image processor for storage, the method comprising:
   a) establishing, with a third computer, a connection to the second computer through a wide area network (WAN) or a local area network (LAN), the second computer having the reduced byte data representation files stored within a memory element;
   b) transmitting through the established connection a request generated by a user from the third computer to the second computer for a selected portion of the reduced byte data representation files stored within the memory element of the second computer, the selected portion of the reduced byte data representation files including a sufficient sample of historical files for an operator to adjust particle analysis and flow cytometer device parameters;
   c) receiving through the established connection the selected portion of the reduced byte data representation files selected with the third computer;
   d) generating with the third computer a viewable reduced byte data representation of the reduced byte data representation files by displaying the selected portion of the reduced byte data representation files in serial order;
   e) determining a functional condition of the flow cytometer based on an evaluation of the sequential display of the reduced data byte representation files as a viewable reduced byte data representation;
   f) remotely adjusting analysis and hardware parameters to optimize the operating condition of the flow cytometer based on the functional condition of the flow cytometer determined in step (e, or remotely trouble shooting the operating condition of the flow cytometer for software or hardware problems based on the functional condition of the flow cytometer determined in step (e.

2. The method of claim 1, further comprising the step of selecting a viewing rate at which to serially view the selected portion of the reduced byte data representation files.

3. The method of claim 2, wherein the step of selecting a viewing rate at which to serially view the selected portion of the reduced byte data representation files further comprises variably adjusting the viewing rate to a decelerated rate.

4. The method of claim 2, wherein the step of selecting a viewing rate at which to serially view the selected portion of the reduced byte data representation files further comprises variably adjusting the viewing rate to an accelerated rate.

5. The method of claim 1, wherein the step of generating a request from the third computer to the second computer for a selected portion of the reduced byte data representation files between a first point in time and a second point in time further comprises selecting a time bound portion of the reduced byte data representation files with a time period selection element.

6. The method of claim 1, wherein the viewable reduced byte data representation comprises an intermittently updated graphical display.

7. The method of claim 6, wherein the intermittently updated graphical display includes one or more of: a chromatogram, computed tomographies, a histogram, and viewable parametric data.

8. The method of claim 7, wherein the viewable parametric data comprises one or more of: sample number, operator identification number, date, drop delay status, temperature status, humidity status, laser power status, network status, particle analysis start time, particle analysis stop time, time elapsed, event rate, total events, particle count, percent particles collected, percent particles aborted, or percent particles coincident.

* * * * *

UNITED STATES PATENT AND TRADEMARK OFFICE
CERTIFICATE OF CORRECTION

PATENT NO. : 10,425,466 B2
APPLICATION NO. : 14/176508
DATED : September 24, 2019
INVENTOR(S) : Salinas et al.

Page 1 of 1

It is certified that error appears in the above-identified patent and that said Letters Patent is hereby corrected as shown below:

On the Title Page

Item (57), should read:
ABSTRACT
Generally, a computer implemented remote monitoring system which generates a viewable reduced byte data representation for each one of a plurality of analyzed instrument signals. Specifically, a flow cytometer remote monitoring system which generates a viewable reduced byte data representation for each one of a plurality of analyzed flow cytometer signals.

Signed and Sealed this
Fourth Day of February, 2020

Andrei Iancu
*Director of the United States Patent and Trademark Office*